United States Patent [19]

Breiter et al.

[11] 4,056,468
[45] Nov. 1, 1977

[54] ISOLATION OF COMPONENT MATERIALS OF AQUEOUS SOLUTIONS SOLUBLE IN LIPOPHILIC SOLVENTS

[75] Inventors: Joachim Breiter; Roland Helger, both of Darmstadt, Germany

[73] Assignee: Merck Patent Gesellschaft mit beschrankter Haftung, Darmstadt, Germany

[21] Appl. No.: 553,023

[22] Filed: Feb. 25, 1975

[30] Foreign Application Priority Data

Mar. 2, 1974 Germany ............................ 2410033

[51] Int. Cl.$^2$ ............................................. B01D 15/00
[52] U.S. Cl. ................................. 210/31 R; 23/230 B
[58] Field of Search ............. 23/230 B; 210/24, 31 C; 210/41, 31 R, 40; 252/449, 451

[56] References Cited

U.S. PATENT DOCUMENTS

| | | | |
|---|---|---|---|
| 3,494,875 | 2/1970 | Page et al. | ............................ 252/449 |
| 3,761,227 | 9/1973 | Conrad et al. | ..................... 23/230 B |
| 3,888,972 | 6/1975 | Kiselev et al. | ....................... 252/449 |

FOREIGN PATENT DOCUMENTS 1,353,861   1/1964   France ................................. 252/449

OTHER PUBLICATIONS

Kesner et al., "Determination of Total Organic Acids in Urine by Extraction with Organic Solvents," *Clinical Chemistry*, vol. 19, No. 6, 1973, pp. 593-596.

*Primary Examiner*—Wilbur L. Bascomb, Jr.
*Assistant Examiner*—Ivars Cintins
*Attorney, Agent, or Firm*—Millen & White

[57] ABSTRACT

Process for the isolation of component materials of aqueous solutions by adsorption of the aqueous solutions on concentration agents based on silica gel and/or kieselguhr and subsequent extraction of the component materials with lipophilic solvents, which employs as concentration agents flowable silica gels and/or kieselguhrs with an average particle size of 0.05 to 1.0 mm., an average pore volume of 0.2 to 3 ml./g., and a specific surface of 0.2 to 50 m$^2$/g.

11 Claims, No Drawings

ISOLATION OF COMPONENT MATERIALS OF AQUEOUS SOLUTIONS SOLUBLE IN LIPOPHILIC SOLVENTS

BACKGROUND OF THE INVENTION

This invention relates to a process for the isolation of component materials of aqueous solutions soluble in lipophilic solvents and to the use of certain concentration agents for the carrying out of the process.

The extraction of such lipophilic solvent-soluble component materials is of increasing importance, especially in diagnosis, where the detection or determination of component materials of body fluids is already carried out to a great extent. In these biological and medicinal investigations, as a rule the component materials to be determined are extracted from the aqueous liquids with the aid of lipophilic solvents. These component materials are thereby separated and thus purified from undesired accompanying materials, e.g., sugars, salts, proteins, urea, frequently present in large excess. By concentration of the thus-obtained extracts, component materials present only in small amounts can also be enriched. In some cases, they are accessible to analytical methods only in this way.

However, the methods previously available are not satisfactory and exhibit considerable disadvantages, especially in the case of extraction of component materials from body fluids, such as urine, blood, serum or extracts or parts of organs or tissues.

In the case of a direct extraction of the aqueous phases with lipophilic solvents, as is known from experience, phase separation is very difficult to carry out since emulsions are frequently formed which cannot be separated or can only be separated with difficulty and thus make a quantitative extraction impossible. Furthermore, the breaking of the emulsions necessitates an additional expenditure of time, which is disadvantageous, especially in the case of serial investigations.

It has previously been attempted to achieve an isolation of these component materials by their absorption from the aqueous solution by a concentration agent. For this purpose, numerous materials have been suggested, e.g., anhydrous sodium and magnesium sulphate, adsorbents based on silicate, such as conventional silica gel or florisil, molecular sieves and ionic cellulose ethers. These concentration agents admittedly possess high water retention capacities but from their mixtures with body fluids, the component materials to be determined cannot be quantitatively extracted due to inclusions, irreversible adsorptions or ion exchange processes. Particularly, the previously employed silicate surface active adsorbents possess the disadvantage that a desorption of the component materials to be investigated is not possible quantitatively with the help of lipophilic solvents as a result of the activity or polarity of the surface of these adsorbents. Polar compounds such as, morphine, may not even be extracted by mixtures of lipophilic and polar solvents without simultaneous desorption of the water.

This applies, e.g., also to the process, described in Clinical Chemistry, pages 593 to 596, 1973, for the determination of organic acids in the urine. This process employs a selective extraction by an adsorption and partition chromatography with one of the activated silica gels usually employed therefor.

The silica gel employed possessed a particle size of 0.05 to 0.2 mm. but the described process shows that, due to the properties of this material, the polar component materials are held back by the silica gel. The non-polar substances are also relatively strongly adsorbed and then only slowly liberated again. This follows, inter alia, from the amounts of solvent necessary for the extraction and their composition of polar and non-polar solvents. Thus, e.g., for 1 part by volume of sample liquid, there are used about 25 parts by volume of solvent. Thus, the silica gel possesses too high an activity. Furthermore, according to this previously known process, a mechanical mixing of the sample liquid with the silica gel is necessary. However, in the case of a subsequent quantitative determination, this is a further source of error. If one attempts to employ the method indicated by way of example for fatty acids for the extraction of pharmaceuticals or of their metabolites with the conventional silica gel, the method does not work. The metabolites and their parent substances of various structure are even adsorbed from the aqueous solution. A desorption only takes place with polar solvents and then with the co-extraction of the water. However, in this way, the desired object of carrying out a purification and concentration of the component materials cannot be achieved.

According to this invention, the disadvantages of the known processes are overcome and a process is made available by which a gentle and quantitative extraction of component materials of aqueous solutions soluble in lipophilic solvents is possible.

It has been found that certain concentrating agents are able to take up the aqueous solutions with the maintenance of their flowability and that the component materials can be obtained quantitatively from these mixtures and surprisingly with very small amounts of solvent. This method is extremely gentle so that neither the aqueous liquids nor the component materials are changed by this treatment. The take up of the aqueous solutions takes place quantitatively since the amount of the concentrating agent is so adjusted that at most the maximum water take up capacity is reached. The subsequent desorption of the component materials from the flowable, charged concentrating agent with lipophilic solvents takes place without problems and quantitatively.

SUMMARY OF THE INVENTION

According to this invention, lipophilic solvent-soluble component materials of aqueous solutions are isolated therefrom by adsorption of an aqueous solution on a silica gel- and/or kieselguhr-based concentration agent and subsequent extraction of the component materials from the aqueous solution while absorbed in the concentrating agent with a lipophilic solvent, employing, as the concentration agent, at least one of a flowable silica gel and a kieselguhr having an average particle size of 0.05 to 1.0 mm., an average pore volume of 0.2 to 3 ml./g. and a specific surface of 0.2 to 50 $m^2$/g.

DETAILED DISCUSSION

It was not foreseen that silica gels and kieselguhrs having the above-defined characteristics would be substantially superior to those previously employed as concentration agents. This was even less to be predicted since other silica gels had been used for this purpose with little or no success. Silica gels or kieselguhrs with other particle sizes, a smaller pore volume or a substantially greater specific surface are not suitable for the process according to the invention. With the concentration agents employed in this invention, one can achieve, for the first time, a quantitative desorption of the component materials, even with the smallest amounts of solvent. There is thus now available an outstanding and almost universally applicable analysis method with high dependability. Due to the use of the concentration agents which are insoluble and non-swellable in water and solvents, which are non-ionic, flowable and percolatable, the extraction can be converted, in almost ideal manner, into a solid/liquid elution. The concentration agents employed in this invention are outstanding phase separation agents and enable a quantitative extraction without the necessity of mechanical mixing processes during loading. They maintain their granularity during the whole process and can, surprisingly, be charged with an amount of aqueous solution up to the limit of their water take up capacity without water being removed therefrom upon elution with the lipophilic solvents.

The pH value of the aqueous phase bound to the concentration agent can also be varied, by the addition of acidic, alkaline or buffer solutions or gaseous acids or bases so that there can be carried out selective elutions, employing also different lipophilic solvents, the selected solvent depending upon the properties of the dissolved materials to be extracted. Furthermore, the aqueous solution bound to the concentration agent can again be forced out by other solutions and, in this way, further investigations can be made accessible.

The concentration agents to be employed are large pored adsorbents based on silicic acid in granular form (granulate or spheroidal agglomerates). They are prepared according to special processes from naturally occurring or synthetic $SiO_2$ modifications. They are, in part, commercially available or the desired parameters are adjusted by processes known in the literature.

The maintenance of definite particle sizes, of the given pore volumes and of the small specific surface is vital. Due to the interplay of these characteristics, effects previously not possible are achieved. Silica gels and kieselguhrs both can be employed, individually or as mixtures. The particle size (particle diameter) of the individual particles of these concentration agents is from 0.05 to 1 mm., preferably from 0.15 to 0.4 mm. It is especially advantageous but not essential to select a particle size distribution which is as narrow as possible, e.g., in which 60% of the particles display particle sizes within a specific range, i.e., 60% or more of all the particles have substantially the same size. The given particle size is decisive for the packing density, the stability and the rate of throughflow of a column packing produced therefrom. The water take up capacity is, in turn, influenced by the packing density.

The concentration agents employed in the process of this invention have a pore volume of at least 0.2 ml./g. The greater is the pore volume, the better are the agents suited for the carrying out of the process. In general, pore volumes of from 0.2 to 3 ml./g. have proved to be particularly useful. Having regard to the volume and the mechanical stability of the granulated material, the preferred pure volumes are from 0.5 to 1.7 ml./g.

Pore volume influences the ability of the concentration agents to take up water which, in turn, is an important factor in determining the suitability of the concentration agents to be employed. The concentration agents of this invention have a water take up capacity of from 0.2 to 1 ml. water/$cm^3$ of packed concentration agent, preferably 0.3 to 0.8 ml./$cm^3$. "Packed" means compacted in a conventional manner, e.g., as in a chromatographic column.

A further important characteristic of the concentration agents according to the invention is their surface activity which can be defined by their specific surface area. Silica gels or kieselguhrs of especially high activity stages do not give satisfactory results in the process of this invention. The specific surface of the particles of the concentration agents of this invention have from 0.2 to 50 $m^2/g$. For silica gels the preferred range is about 0.3 to 20 $m^2/g$. For kieselguhrs, the preferred range is about 0.5 to 5 $m^2/g$. Silica gels with average pore diameters of about 500 to 40,000 A have relatively small specific surfaces but in the case of kieselguhrs, normally more than 65% of the pore diameters are above 40,000 A. Only with these materials, which are relatively inactive as normal adsorption agents, is it possible to achieve the quantitative extractions to be achieved according to the invention.

Such concentration agents are, in part, produced from natural products and, depending upon origin, may contain interfering impurities, e.g., iron salts or organic compounds. Testing for purity, as a rule, is by thin layer chromatography and UV spectroscopy. Insofar as a purification is necessary for a specific component material, this can be achieved most simply in known manner by washing with hydrochloric acid, methanol and/or water.

The concentration agents employed in the process of this invention can, as a result of their high water retention capacity, take up liquids without difficulty. Surprisingly, the mixing takes place without mechanical action so that a stirring or shaking up is not needed. The loading of the concentration agent with aqueous solution can be up to the maximum water retention capacity of the selected concentration agent. Depending upon the packing weight of the concentration agent, the capacity limit is, in general, achieved when the aqueous solutions are mixed with the concentration agents roughly in a weight ratio of water to kieselguhr of from 1:0.4 to 1:1.25 or of water to silica gel of from 1:0.9 to 1:1.7. Corresponding ratio ranges between these two ranges can be employed when mixtures of kieselguhr and silica gel are employed, the exact values depending on the proportion of the two in the mixture. Since, in the case of the elution, residues of the lipophilic solvent remain behind, which leads to losses, the use of smallest amounts of concentration agents possible is usually preferred.

The desired component materials are then extracted from these flowable, laden concentration agents with a lipophilic solvent. This extraction can take place according to all known methods of a liquid/solid extraction, e.g., in the batch process or continuously, e.g., in a column. The extracts obtained are clear solutions and completely free from emulsions. The component materials adsorbed from the starting aqueous solution which are soluble in lipophilic solvents are extracted quantitatively from the concentrating agent.

As lipophilic solvents, there can be employed all which are suitable for the dissolving of the component materials to be extracted. By lipophilic solvents, there are here to be understood all the organic solvents which readily dissolve fats, oils and fat-like substances. Such solvents are e.g., ethers, such as diethyl ether and diisopropyl ether; esters, such as methyl acetate and ethyl acetate; alcohols, such as methanol, ethanol, propanol, isopropanol, butanol and higher homologues; halogenated hydrocarbons, such as dichloromethane, chloroform, tetrachloromethane, 1,2-dichloroethane and 1,1,2-trichloroethane; and aromatic and aliphatic hydrocarbons, e.g., benzene, toluene, pentane, hexane, heptane, petroleum ether and cyclohexane. All these solvents can be used alone or in admixture. In principle, all organic solvents can be used which also according to the previously known processes have been regarded as suitable for the dissolving of the component materials from aqueous solutions. A special advantage of the concentration agents employed in the process of this invention consists in the possibility of using for the extraction lower aliphatic alcohols, e.g., organic solvents miscible with water. In this way, in many cases, the quantity of the necessary amount of solvent is reduced. One can e.g., achieve quantitative extractions with amounts of solvent which, from the point of view of volume, are about the same as the volume of the starting aqueous solution. This was hitherto not possible. In the case of mixtures of the water-miscible solvents with water-insoluble solvents (e.g., chloroform/isopropanol 80/20 vol. %) if the proportion of the water-miscible solvent is not too high (<30 vol. %), a satisfactory extraction is achieved with the water surprisingly remaining bound in the concentration agent. Furthermore, according to a special embodiment of the process of this invention, extractions can also be carried out if necessary with, e.g., lower aliphatic alcohols alone or in admixture with a small proportion of a water-insoluble lipophilic solvent. These lower aliphatic alcohols are able to split component materials of serum, e.g., triglycerides bound to protein, bound to the concentration agents. The triglycerides thereby become extractable. Small amounts of water possibly co-extracted in the case of this process are unimportant in the subsequent analysis.

The process according to the invention has special importance for the investigation of body fluids, especially urine, blood, plasma and serum, as well as gastric juice, lymph fluids, brain and spinal fluid. Furthermore, aqueous fluids are also of importance which have been obtained from tissue material or parts of organs. However, in addition, any other desired aqueous solutions can also be extracted, e.g., extracts from plants and drugs (e.g., opium tinctures, extracts of hashish and tobacco), as well as wash liquids and waste waters. From all of these fluids, the component materials soluble in lipophilic solvents can be isolated quickly, satisfactorily and quantitatively.

The process according to the invention has special importance in diagnosis and for testing of body fluids for their content of pharmaceuticals, drugs, toxic materials or pharmaceutical metabolites. Thus, e.g., according to the process of this invention, there have already been detected and determined analgesics, sedatives, hypnotics, anti-epileptics, psychopharmaceuticals, sympathicomimetics, anti-histaminics, narcotics, alkaloids and antibiotics or their metabolites. However, in addition, there have also been extracted and investigated metabolites natural to the body, e.g., lipids, triglycerides, fatty acids, steroids and porphyrins.

In some cases, it is expedient to convert the component materials present in the body fluids, by a pH change, into the undissociated and consequently into a form more soluble in the lipophilic solvents. Enzymatic splittings, e.g., of conjugated metabolites, such as glucuronides and sulphates, can also be carried out in the aqueous solution to be investigated, e.g., after being brought together with the concentration agent. Since the concentration agent to be employed according to the invention is neutral and insensitive to pH value changes, there can be applied thereto any desired aqueous solution. In the extracts obtained, there can be detected and determined the component materials of the initial aqueous solutions according to methods known and described in detail in the literature. In many cases, it is especially advantageous to prepare, with the help of lipophilic solvents, a solution whose volume corresponds to that of the original sample, since the values obtained for the component materials are then identical with those of the aqueous solution. It is, of course, also possible according to the process of this invention, to prepare lipophilic solvent solutions with substantially higher concentrations of the sought component materials, whereby the detection or the determination of these materials can be made substantially easier. For this purpose, e.g., several extracts can be concentrated and combined.

The extracts obtained are especially suitable for gas and thin layer chromatographic detection of the component materials. However, all other known detection and determination methods can also be employed, e.g., photometric or colorimetric methods as well as fluorimetric, immunologic and radioimmunologic methods.

In many cases, by the process of this invention, standardized processes for the determination of particular component materials of aqueous solutions are possible. In order to make this standardization easier and also to make possible large-scale tests, the concentration agents according to the invention are expediently offered in particular finished packings. The finished packings contain the concentration agents in amounts of about 0.5 to 50 g., whereby the amount is adjusted to the intended purpose of use. Although the packing can be in any desired form, e.g., pillow- or sphere-shaped bags, column packings, e.g., glass or synthetic resin columns of about 5 to 20 cm. length and a diameter of 1 to 3 cm., are preferred.

Also suitable are, e.g., plastic single-use syringes commercially available for injection purposes, if a lipophilic solvent is selected to which the synthetic resin material is stable. The aqueous solution then only needs to be applied to or drawn into such a syringe packed with the concentration agent, so that mixing with the concentration agent occurs spontaneously. In this form, the adsorbed sample is readily transportable. The extraction of the component materials from the concentration agent can be conducted centrally at another place. The transport of liquid samples intended for the investigation is, in this way, considerably simplified. This makes easier screening programs and large scale investigations for the testing for the misuse of pharmaceuticals or drugs.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Elution With Chloroform and Chloroform/Ethyl Acetate

Two glass columns of 1 cm. diameter (blocked at their outlet with glass wool) were each uniformly filled with 5 g. of a granulated kieselguhr with a particle size of about 0.125 to 0.4 mm. The specific surface of the kieselguhr was about 1 m²/g., its pore volume was about 0.3 ml/g., and its water retention in the column was about 1 ml/g.

To each column were applied 5 ml. of a urine which contained codeine, diphenhydramine, amphetamine and morphine in concentrations each of 20 μg./ml. and which had been adjusted to pH 9 with NH$_4$Cl/NH$_3$ buffer. The liquid was quickly soaked up by the kieselguhr.

One of the columns was eluted with 50 ml. of chloroform, the other with 50 ml. of a mixture of equal parts of chloroform and ethyl acetate. In both cases, the eluate was completely clear and the water remained bound to the column. The eluates were each divided into successive 10 ml. fractions and evaporated. The residues were investigated by thin layer chromatography. In the case of the sample eluted with pure chloroform, codeine, diphenhydramine and amphetamine were completely contained in the first 10 ml. fraction but only about 70% of the morphine, the remainder being in the second fraction. The third and the following fractions contained no residues.

When the columns were eluted with chloroform/ethyl acetate, all substances, including morphine, were completely eluted in the first 10 ml. fraction.

EXAMPLE 2

Quantitative Comparison of Extraction Via Column and Three-stage Liquid-liquid Extraction For these investigations, there was used a solution of 1 mg. Na-barbital in 100 ml. 1M (ammonium chloride/tartaric acid) buffer of pH 2. As concentration agent, there was used an agglomerated kieselguhr with particle sizes of 0.15 to 0.40 mm., a specific surface of about 1 m²/g., corresponding to an average pore diameter (>80%) of >40,000 A and a pore volume of 1.1 ml/g. As columns, there were used 50 ml. single-use polypropylene syringes having funnel-shaped run-off attachable canule. The run-off was blocked by a wick of cotton batting.

14 g. of the concentration agent was poured into each column and shaken down. The columns, with a diameter of 27 mm., were filed to a height of 80 mm. The top of the column bed was closed off with a fine-holed mesh of polypropylene, held by a ring of polypropylene. To each column were applied 20 ml. of barbital-containing buffer (ammonium chloride/tartaric acid) solution, which was soaked up immediately by the kieselguhr. Each of 2 columns were eluted with diethyl ether, 2 others with chloroform. With the help of attachable canules on the run-off, the throughflow was regulated so that 20 ml. elution agent passed through the column in 10 minutes. The eluates were divided into successive 20 ml. fractions. About 15 ml. of elution agent remained behind with the aqueous phase on the concentration agent. Not only the ether but also the chloroform eluates were clear. All eluate fractions were blown with nitrogen to dryness on a waterbath.

For comparison, 20 ml. amounts of barbital solution were each extracted three times with 40 ml. ether or chloroform in a separating funnel and the extracts were filtered over phase separation paper and blown dry with nitrogen.

The absorbances at 255 nm of the residues of the liquid-liquid extraction and those obtained from the eluates from the columns were determined quantitatively by UV spectroscopy in acidic and alkaline solution according to the usual determination methods for barbiturates. In Table I are given the extraction or elution yields for both solvents.

TABLE I

|  | Elute Fraction | | | | Consumption of |
|---|---|---|---|---|---|
|  | 1st | 2nd | 3rd | Total | Solvent |
| Elution (concentration agent) | 99% | — | — | 99% | 35 ml. ether |
| Extraction (liquid/liquid) | 85% | 13% | — | 98% | 80 ml. ether |
| Elution (concentration agent) | 81% | 16% | — | 97% | 55 ml. chloroform |
| Extraction (liquid/liquid) | 69% | 20% | 5% | 94% | 120 ml. chloroform |

The continuous extraction employing the concentration agent required for corresponding yields compared with liquid-liquid extraction, less than half the amount of solvent. In the case of ether, the extraction of bartital was practically quantitative in the first 20 ml. eluate fraction.

EXAMPLE 3

Quantitative Comparison of Two Concentration Agents in the Case of the Extraction of Polar and non-polar Alkaloids The columns employed are those described in Example 2. The solution to be extracted was a urine sample, pH 9.3, buffered with ammonium chloride/ammonia, which contained 20 μg. each of morphine and codeine dissolved in 20 ml. The elution agent was a mixture of dichloromethane/isopropanol (85/15). The eluates were divided into fractions, each of 20 ml. A very light turbidity in the second fraction disappeared upon concentration of the solution.

For comparison, a 20 ml. sample of urine was extracted in a separating funnel twice with 40 ml. portions of solvent (liquid-liquid extraction). The eluates and extracts were, after evaporation of the solvent, quantitatively investigated gas chromatographically for their morphine and codeine contents.

As concentration agents, there were used:

a. 14 g. of the granulated kieselguhr described in Example 2.

b. 26 g. of a wide-pored, granulated spheroidal silica gel which occupied the same volume as the kieselguhr according to a) with particle sizes between 0.15 and 0.30 mm, a specific surface of 0.8 m²/g., an average pore diameter of 40,000 A, and a pore volume of 0.7 ml./g.

Table II shows the distribution of morphine and codeine in the first and second 20 ml. eluate fractions. The yield after two liquid-liquid extractions, each with 40 ml. solvent, was taken as 100%.

TABLE II

| Concen-tration Agent | MORPHINE Fraction | | | CODEINE Fraction | | |
|---|---|---|---|---|---|---|
| | 1st | 2nd | Total | 1st | 2nd | Total |
| a) μg | 15.9 | 4.8 | 20.7 | 17 | 0.8 | 17.8 |
| kieselguhr % | ≙ 76 | ≙ 23 | ≙ 99 | ≙ 95 | ≙ 4.5 | ≙ 99.5 |
| b) μg | 19.9 | 1.3 | 21.2 | 17.6 | 0.1 | 17.7 |
| silica gel % | ≙ 96 | ≙ 6 | ≙ 102 | ≙ 98.3 | ≙ 0.6 | ≙ 99 |
| Extraction 2 × 40 ml. CH$_2$Cl$_2$/isopropanol (85/15) | μg % | | 20.8 ≙ 100 | | | 17.9 ≙ 100 |

| Solvent Consumption: | Elution | | |
|---|---|---|---|
| | 1st Fraction 35 ml. | 2nd Fraction 20 ml. | Liquid/Liquid Extraction 80 ml. |

EXAMPLE 4

Extractability at pH 2 and 9

Following the procedures of Examples 2 and 3, the following toxicologically important pharmaceuticals and drugs were investigated at pH 2 and pH 9 for their extractability with the new concentration agents:

| Extractable at pH 2 | Extractable at pH 9 |
|---|---|
| hexobarbital | thioridazine |
| thiopental | promethazine |
| amobarbital | levomepromazine |
| phenobarbital | amitryptilin |
| cyclobarbital | 4-aminophenazone |
| hydroxypentobarbital | 4-dimethylaminophenazone |
| secobarbital | pentazocine |
| pentobarbital | methadone |
| heptabarbital | tilidine |
| brallobarbital | propoxyphen |
| methylphenobarbital | meperidine |
| barbital | oxycodon |
| carbromal | morphine |
| bromural | hydromorphone |
| acecarbromal | quinine |
| ethinamate | ethylmorphine |
| methaqualone | cocaine |
| glutethimide | codeine |
| diphenylhydantoin | nicotine |
| meprobamate | papaverine |
| oxazepam | mescaline |
| medazepam | diphenylhydramine |
| chlordiazepoxide | norephedrine |
| diazepam | phenmetrazine |
| nitrazepam | ephedrine |
| phenactin | amphetamine |
| paracetamol | methamphetamine |
| salicylic acid | chlorpheniramine |
| | mephentermine |
| | methylphenidate |

The lipophilic extraction solvent in each case was dichloromethane/isopropanol (85/15 vol. %). The evaluation took place in some cases by thin layer chromatography and in others by UV-spectroscopy.

Using 20 ml. samples of urine, the basic substances were extracted at pH 9 with 35 ml. solvent in yields of 90 to 100%. Ephedrine, amphetamine and morphine were extracted in yields of 70 to 90%. The barbiturates and the other sleeping agents showed corresponding extraction rates of 80 to 100% at pH 2. In all cases, elution with a further 20 ml. of solvent achieved 100% extraction.

EXAMPLE 5

Methaqualone Detection in Urine

A urine sample of a patient who had taken an overdose of a methaqualone-containing pharmaceutical was heated for 15 minutes with concentrated hydrochloric acid. There resulted a black, flocculant solution which was adjusted to pH 9.5 with concentrated aqueous sodium hydroxide solution. 20 ml. of this sample were, without filtering off the precipitate, applied to a single use syringe as described in Example 2 which was filled with 16 g. kieselguhr (particle size 0.15 to 0.40 mm., specific surface 1 m$^2$/g., pore volume 0.64 ml./g.), which was then eluted with 35 ml. dichloromethane/isopropanol (80/20). The clear eluate (20 ml.) was blown dry with nitrogen. The residue was chromatographed on a silica gel finished plate with the eluting agent chloroform/acetone (80/20). The metabolite pattern of methaqualone was clearly found.

In the case of the extraction of the same urine with the same solvents in a separating funnel, there resulted a thick emulsion which could only be broken by centrifuging. The extract was substantially more colored by urine pigments than the one obtained from the concentration agent, so that the chromatographic detection was considerably disturbed.

EXAMPLE 6

Using the columns and concentration agents described in Example 2 and elution with 35 ml. dichloromethane/isopropanol (85/15), the acidic and basic substances mentioned in Example 4 can be extracted from 20 ml. samples of urine at pH 8.5 to 9 in yields of 80 to 100% at pH 8.5 to 9. The barbiturate metabolites, which are eluted only in about 50% yield, are the sole exception.

In the case of mass screening for drugs and misused pharmaceuticals, the ability to extract both acidic and basic materials from urine in amounts sufficient for the detection by a single extraction is a particular advantage.

EXAMPLE 7

10 ml. Opium tincture was extracted at pH 9 analogously to Example 3. Subsequent thin layer chromatography of the eluate obtained on silica gel finished plates with ethyl acetate/methanol/ammonia (85/10/5) as the eluting agent, produced the typical spot pattern of the opium.

EXAMPLE 8

0.1 Ml. of hydrochloric acid solution of diphenhydramine, amphetamine, morphine and codeine was pipetted into 10 ml. of serum. The concentrations thereof in the serum were 50, 50, 50 and 25 μg./10 ml., respectively. A plastic column with conical run-off (diameter 15 mm., length 150 mm.) was charged with 4 g. granulated kieselguhr (particle size 0.15 to 0.40 mm., pore volume 0.9 ml/g., specific surface > 1 m$^2$/g.) and loaded with 5 ml. serum. After 15 minutes, the serum was completely soaked up. The column was eluted with 15 ml. dichloromethane in 10 minutes, the eluate evaporated and the residue analyzed semi-quantitatively by thin layer chromatography. Diphenhydramine, codeine, amphetamine were completely eluted and morphine in about 90% yield.

EXAMPLE 9

A 10 ml. sample of whole blood of a patient with barbiturate poisoning was mixed in a closable 50 ml. single use syringe with 10 g. of a granulated and washed kieselguhr (particle size 0.2 to 0.5 mm., pore volume 0.63 ml/g., specific surface about 1 m$^2$/g.). The mixture was shaken. The resultant column bed could be eluted, without hindrance, with alcohol-free solvents. 40 ml. chloroform were used for the elution. The eluate was clear. After evaporation of the solvent, the residue was taken up in 0.5 N aqueous sodium hydroxide solution and investigated in the usual way by UV-spectroscopy at 255 nm., which showed a barbiturate concentration of 1.8 mg./100 ml.

EXAMPLE 10

The barrel of a 50 ml. single-use plastic syringe was filled with 14 g. granulated kieselguhr (particle size 0.15 to 0.40 mm., pore volume 1.1 ml./g., specific surface 1 $m^2/g$.). 20 ml. of a urine sample which contained barbiturates and morphine were adjusted to pH 2 with concentrated HCl and applied to the column. After the kieselguhr soaked up the urine, it was eluted with 40 ml. dichloromethane. The eluate showed, at the end, a slight turbidity, but no separation of water. At the end of the elution in the acidic medium, air mixed with ammonia was sucked through the column. The first sucked off residue of dichloromethane was discarded. After a few minutes, ammonia emerged at the lower end of the column. The aqueous phase on the concentration agent was alkaline (pH 10). The column was next eluted with 40 ml. dichloromethane/isopropanol (85/15). Both eluates were evaporated and investigated by thin layer chromatography. The comparison with a two-stage liquid-liquid extraction at pH 2 and pH 9 showed that the elution was selective. Only the acidic extract contained barbiturate, and only the alkaline one contained morphine. The elution yield in the acidic range was 100% and in the alkaline range, > 90% in the case of morphine.

EXAMPLE 11 a. The urine extracted twice according to Example 10 was to be tested for the non-extractable, conjugated proportion of morphine. For this purpose, the aqueous phase had to be expelled from the concentration agent, which was accomplished, after the extraction with dichloromethane/isopropanol, with 35 ml. of a saturated common salt solution applied to the column. The residual solvent and urine solution contained in the column bed were forced out by the concentrated salt solution. There were obtained 20 ml. of a yellow-colored aqueous solution. This was mixed with 20 ml. 25% HCl, heated under reflux and then extracted analogously to Example 10. The morphine content of the eluate was determined.

b. Analogously to Example 11 a), the acidically eluated urine was expelled from the column with 35 ml. saturated ammonium chloride/ammonia buffer (pH 9.5). There were obtained 20 ml. of an aqueous solution having a pH of 8.8. This was again applied to a dry column with the granulated kieselguhr described in Example 10 and eluted with dichloromethane/isopropanol (85/15). Morphine could be detected in the eluate.

EXAMPLE 12

A plastic column with conical run-off (diameter 1 cm., filling volumn 12 ml.) was filled with 1.5 g. spheroidal, widepore silica gel (particle size 0.15 mm. to 0.5 mm., specific surface 0.3 $m^2/g$., pore volume 0.7 ml/g.) to a height of 4 cm. 0.5 ml. serum were pipetted thereon and left to soak in for 10 minutes. It was now eluted with 7 ml. ether/ethanol (3:1) in 10 minutes. The first 4 ml. of the eluate were collected. An aliquot part (0.4 ml.) of this was pipetted off and the triglycerides contained therein were split in known manner with KOH. The liberated glycerol was oxidized to formaldehyde, which was measured quantitatively by condensation with acetylacetone. Triolein, which was treated like the serum sample, served as standard.

In 5 collected area, there was determined a content of triglycerides of 160, 155, 145, 145 and 120 mg./100 ml.

EXAMPLE 13

A 25 ml. sample of urine of a drug addict was adjusted to pH 5 with 2 ml. 0.5 M sodium acetate buffer pH 5.5 and mixed with 5 mg. urease (4 U/mg.). 20 ml. of this solution were applied to a column with granulated kieselguhr analogously to Example 10. The column was closed and stored overnight. After this time, the adsorbed urine possessed a pH value of 9. Subsequently, it was eluted with dichloromethane/isopropanol analogously to Example 10. The basic materials cocaine, benzoylecgonine and morphine contained in the eluate were separated and detected by thin layer chromatography.

EXAMPLE 14

A urine sample was investigated after a poisoning with methaqualone, which is excreted in the urine as a conjugate insoluble in organic solvents but which is converted into extractable form by heating with hydrochloric acid or by enzymatic hydrolysis.

10 ml. of the urine sample were mixed with 1.5 ml. 2 M Na-acetate buffer pH 5.5 and 0.1 ml. aryl sulphatase/ glucuronidase and applied to a plastic column with 8 g. granulated kieselguhr (particle size 0.15 to 0.5 mm., pore volume 1.1 ml./g., spec. surface 1.5 $m^2/g$.). The column was closed and stored for 8 days. After this time, without further pre-treatment, the column was eluted with 20 ml. of chloroform.

Simultaneously, another portion of the same urine sample was heated with hydrochloric acid and, as described in Example 5, extracted with a concentration agent, which was then eluted.

The eluates obtained according to both methods were compared by means of thin layer chromatography and by UV spectroscopy at 235 and 275 nm (in 2 N HCl). In thin layer chromatography, both methods gave the same metabolite pattern with comparable intensity.

Comparison of the extinctions at 235 nm and 275 nm showed that with enzymatic hydrolysis, a 1.3 fold amount of extractable metabolites were liberated compared to hydrolysis with hydrochloric acid.

This kind of enzymatic hydrolysis thus represents an excellent preparation of the samples for the extraction since many materials are excreted in the urine as conjugates.

EXAMPLE 15

Plastic columns according to Example 12 were filled 4.7 cm. in height with the wide-pore silica gel according to Example 3b. At the bottom of the column, a filter disk impregnated with a hydrogen carbonate buffer of pH 10.5 was placed before the exit. These columns were used for the determination of the estrogen contents in urine samples.

To each of two 2 ml. samples of urine of pregnant women was added 0.3 ml. of 37% HCl and the mixtures were heated for 1 hour to 100°. To both samples were added 0.5 ml. of aqueous ammonia (25%). Then, 0.2 ml.

of an estriol standard solution (100 μg/ml.) was added to one sample and 0.2 ml. ethanol was added to the other. 1 ml. of each of these solutions was put onto the column and the elution was done with 6 ml. of ether. 0.2 ml. of a 2% hydroquinone solution in ethanol were added to the eluate and they then were evaporated to dryness. The determination was effected in a manner known as such, namely by heating with sulfuric acid. (Mitteilungen der Deutschen Gesellschaft fuer Klinische Chemie (3), 1970, page 9). In 4 samples of urine, the following estrogen values were found in 24 hours: 14.3, 19.4, 10.2 and 21.9 mg. estriol, respectively.

EXAMPLE 16

A combination of multiple extractions for the isolation and purification of compounds, for example, those contained in blood, can be achieved by the combination of two extraction columns.

For this purpose, a 50 ml. syringe, filled with 16 g. kieselguhr according to Example 2 and in followup, a 2 ml. syringe filled with 0.5 g. of the same kieselguhr, were used. The small syringe was closed at the upper end by a stopper such as used for freeze-dried ampoules. The large column was equipped with a cannula at the outlet. After penetrating the stopper with this cannula, the eluate from the larger column flowed through the bed of the following smaller column.

To 4 ml. of fresh EDTA blood, 1 ml. of 0.025% solution of papaverine hydrochloride and 15 ml. of 0.025% aqueous ammonia was added. After 15 minutes, hemolysis was complete.

The blood thus prepared was loaded onto the larger column. The smaller column was loaded with 0.5 ml. of 0.2 N-sulfuric acid and conjunction between both the columns was effected. After 10 minutes, the larger column was eluted by 50 ml. ethyl acetate. The papaverine thus extracted from the larger column, was re-extracted when flowing through the second column into the sulfuric acid. The eluate (33 ml. after 20 min.) was discarded.

The columns were detached from each other and the aqueous phase in the smaller column was brought to a pH of 9.5 with gaseous $NH_3$ in accordance with Example 10. The column was eluted with 3.5 ml. ethyl acetate. The eluate was extracted with 4 ml. 1N hydrochloric acid and the upper phase was discarded. The acidic solution was measured in a spectrophotometer in 309 nm. in comparison to an extract from blood without added papaverine. The concentration found in the sample with papaverine hydrochloride was 232 μg., i.e., 92.1% of that added to the blood.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the isolation of lipophilic solvent-soluble components from an aqueous solution containing lipophilic components comprising contacting the aqueous solution with one or both of a silica gel-based or kieselguhr-based concentration agent to absorb said aqueous solution therein and subsequently extracting substantially only the lipophilic solvent-soluble components from the aqueous solution absorbed in the concentration agent with a lipophilic solvent, the improvement which comprises employing as the concentration agent a flowable silica gel of kieselguhr or a mixture thereof, having an average particle size of 0.05 to 1.0 mm., an average pore volume of 0.2 to 3 ml./g. and a specific surface to 0.2 to 50 m²/g., and said extracting is conducted without substantial simultaneous desorption of the water of said absorbed aqueous solution, said lipophilic solvent-soluble components being at least one analgesic, sedative, hypnotic, anti-epileptic, psychopharmaceutical, sympathicomimetic, anti-histamine, narcotic, alkaloid, antibiotic, lipid, triglyceride, fatty acid, steroid or porphyrin.

2. A process according to claim 1, wherein the concentration agent is a silica gel with an average particle size of 0.15 to 0.4 mm., an average pore volume of 0.5 to 1.7 ml./g. and a specific surface of 0.3 to 20 m²/g.

3. A process according to claim 2 wherein the specific surface of the silica gel is not more than 0.8 m²/g.

4. A process according to claim 2 wherein said silica gel has a specific surface of 0.8 m²/g., an average pore diameter of 40,000 angstroms and a pore volume of 0.7 ml./g.

5. A process according to claim 1, wherein the concentration agent is a kieselguhr with an average particle size of 0.15 to 0.4 mm., an average pore volume of 0.5 to 1.7 ml./g. and a specific surface of 0.5 to 5 m²/g.

6. A process according to claim 1, wherein the aqueous solution is a body fluid.

7. A process according to claim 6, wherein the body fluid is a sample of urine.

8. A process according to claim 1, wherein the weight ratio of aqueous solution to concentration agent is from 1:0.4 to 1:1.25 for kieselguhr and from 1:0.9 to 1:1.7 for silica gel.

9. A process according to claim 1, wherein the solvent is a water immiscible organic solvent or mixtures thereof or is a mixture of water immiscible and water miscible organic solvents.

10. A process according to claim 9, wherein the water immiscible solvent is a chlorinated alkane and the water miscible solvent is isopropanol.

11. A process according to claim 1, wherein a measured amount of the concentration agent is packaged in a single-use container adapted to store the concentration agent with the aqueous solution adsorbed thereon prior to extraction of the lipophilic-soluble components from the aqueous solution absorbed in the concentration agent with a lipophilic solvent.

* * * * *